(12) United States Patent
Avinash et al.

(10) Patent No.: US 7,970,203 B2
(45) Date of Patent: Jun. 28, 2011

(54) PURPOSE-DRIVEN DATA REPRESENTATION AND USAGE FOR MEDICAL IMAGES

(75) Inventors: Gopal Biligeri Avinash, Menomonee Falls, WI (US); Saad Ahmed Sirohey, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 1128 days.

(21) Appl. No.: 11/725,244

(22) Filed: Mar. 19, 2007

(65) Prior Publication Data

US 2008/0232718 A1 Sep. 25, 2008

(51) Int. Cl.
  G06K 9/00 (2006.01)
  G06K 9/34 (2006.01)
  G06K 9/40 (2006.01)
(52) U.S. Cl. ........ 382/154; 382/128; 382/173; 382/274; 375/240.19
(58) Field of Classification Search .................. 382/154, 382/128, 130, 131, 132, 240, 232, 239, 244, 382/250, 256, 270, 272, 299, 298, 276, 173, 382/274; 378/37, 901; 709/203, 217, 201; 375/240.18, 240.19, 240.24, 240.29, 240.23, 375/240.08
See application file for complete search history.

(56) References Cited

U.S. PATENT DOCUMENTS

| | | | |
|---|---|---|---|
| 5,333,212 A | 7/1994 | Ligtenberg | |
| 5,502,778 A | 3/1996 | Ishikawa et al. | |
| 5,796,862 A | 8/1998 | Pawlicki et al. | |
| 6,144,772 A * | 11/2000 | Garland et al. | 382/239 |
| 6,633,674 B1 | 10/2003 | Barnes et al. | |
| 6,704,440 B1 | 3/2004 | Kump | |
| 6,771,822 B1 | 8/2004 | Brackett | |

(Continued)

OTHER PUBLICATIONS

Krishnan, Karthik; "Efficient Transmission of Compressed Data for Remote Volume Visualization"; IEEE Transactions on Medical Imaging, vol. 25, No. 9, pp. 1189-1199; Sep. 2006.*

(Continued)

Primary Examiner — Sheela C Chawan
(74) Attorney, Agent, or Firm — Fletcher Yoder

(57) ABSTRACT

A technique for selecting portions of a multi-resolution medical image data set to be stored and the portions of the multi-resolution medical image data set to be discarded in order to reduce the overall amount of image data that is stored for each image data set. The selection is based on the clinical purpose for obtaining the medical image data. The clinical purpose for obtaining the medical image is used to define regions of interest in the medical image. At each resolution level of the multi-resolution medical image data set, the regions of interest are stored at the full resolution, while the remaining portions of the medical image are stored at a lesser resolution. A three-dimensional bit mask of the regions of interest is produced from a segmentation of the regions of interest. The segmentation list and the multi-resolution medical image data set are decomposed into multiple resolution levels. Each resolution level has a low frequency component and several high frequency components. The low frequency portions at each resolution level may be stored in their entirety. The segmentation list is used to select the regions in the high frequency portions of the multi-resolution image data that correspond to the regions of interest and those regions that do not. The regions in the high frequency portions of the multi-resolution image data that correspond to the region of interest are stored. Those regions in the high frequency portions of the multi-resolution image data that do not correspond to a region of interest are discarded.

17 Claims, 11 Drawing Sheets

U.S. PATENT DOCUMENTS

| | | | |
|---|---|---|---|
| 6,891,973 | B1 | 5/2005 | Atsumi et al. |
| 6,912,319 | B1 | 6/2005 | Barnes et al. |
| 6,937,767 | B1 | 8/2005 | Burak et al. |
| 7,236,637 | B2 * | 6/2007 | Sirohey et al. ............ 382/240 |
| 7,421,136 | B2 * | 9/2008 | Sirohey et al. ............ 382/240 |
| 2002/0044696 | A1 * | 4/2002 | Sirohey et al. ............ 382/240 |
| 2002/0090140 | A1 | 7/2002 | Thirsk |
| 2003/0026488 | A1 | 2/2003 | Park et al. |
| 2004/0008894 | A1 | 1/2004 | Zeineh |
| 2004/0022447 | A1 | 2/2004 | Mukhopadhyay et al. |
| 2004/0071356 | A1 | 4/2004 | Sudharsanan et al. |
| 2004/0264794 | A1 | 12/2004 | Nister et al. |
| 2007/0065018 | A1 | 3/2007 | Thiagarajan |
| 2008/0232699 | A1 | 9/2008 | Gering et al. |
| 2008/0232701 | A1 | 9/2008 | Gering et al. |

OTHER PUBLICATIONS

Stoem, Jacob, et al.; "Medical image compression with lossless regions of interest," Signal processing 59 (1997), 155-171.

Jia, Wenjing, et al.; "Echocardiography sequential images compression based on region of interest," ICITA 2004, 232-236.

Park, et al.; "Region-of-interest Coding Based on Set Partitioning in Hierarchical Trees," IEEE Trans. On Circuits and Systems for Video Technology, v. 12, Feb. 2002, pp. 106-113.

* cited by examiner

PURPOSE-DRIVEN DATA REPRESENTATION AND USAGE FOR MEDICAL IMAGES

BACKGROUND

The invention relates generally to the field of medical image data storage. More particularly, the invention relates to a technique for reducing the amount of medical image data of a medical image data set that is stored in long-term storage.

Picture archiving and communications systems, or PACS, have become an extremely important component in the management of digitized image data, particularly in the field of medical imaging. Such systems often function as central repositories of image data, receiving the data from various sources, such as medical imaging systems. The image data is stored and made available to radiologists, diagnosing and referring physicians, and other specialists via network links. Improvements in PACS have led to dramatic advances in the volumes of image data available, and have facilitated loading and transferring of voluminous data files both within institutions and between the central storage location and remote clients.

In the medical diagnostics field, depending upon the imaging modality, digitized data may be acquired and processed for a substantial number of images in a single examination, each image representing a large data set defining discrete picture elements (pixels) of a reconstructed image, or volume elements (voxels) in three dimensional data sets. Computed tomography (CT) imaging systems, for example, can produce numerous separate images along an anatomy of interest in a very short examination timeframe. Other imaging modalities are similarly capable of producing large volumes of useful image data, including magnetic resonance imaging (MRI) systems, digital X-ray systems, X-ray tomography systems, ultrasound systems, positron emission tomography (PET) systems, and so forth. Ideally, all such images are stored centrally on the PACS, and made available to the radiologist for review and diagnosis.

Various techniques have been proposed and are currently in use for analyzing and compressing large data files, such as medical image data files. Image data files typically include streams of data descriptive of image characteristics, typically of intensities or other characteristics of individual pixels or voxels in the reconstructed image. In the medical diagnostic field, these image files are typically created during an image acquisition, encoding or processing (e.g., reconstruction) sequence, such as in an X-ray, MRI, CT, or other system, or in a processing station designed to process image data from such systems. The image data may be subsequently processed or reprocessed, such as to adjust dynamic ranges, or to enhance certain features shown in the image, for storage, transmittal and display.

While image files may be stored in raw and processed formats, many image files are quite large, and would occupy considerable disc or storage space. The almost exponential increases in the resolutions of imaging systems that has occurred and which appears will continue into the future is leading to the creation of ever larger image files, typically including more data as a result of the useful dynamic range of the imaging system, the size of the matrix of image pixels and voxels, and the number of images acquired per examination. In addition, the processing and memory requirements for current PACS systems for new clinical applications and techniques is beginning to tax current system capabilities, such as the ever increasing clinical needs for volumetric data sampled over time and for the use of multiple energy volumes for better visualization of anatomical and functional features.

In addition to occupying large segments of available memory, large image files can be difficult or time consuming to transmit from one location to another. In a typical medical imaging application, for example, a scanner or other imaging device will typically create raw data which may be at least partially processed at the scanner. The data is then transmitted to other image processing circuitry, typically including a programmed computer, where the image data is further processed and enhanced. Ultimately, the image data is stored either locally at the system, or in the PACS for later retrieval and analysis. In all of these data transmission steps, the large image data file must be accessed and transmitted from one device to another.

Current image handling techniques include compression of image data within the PACS environment to reduce the storage requirements and transmission times. Such compression techniques generally, however, compress entire files, including descriptive header information which could be useful in accessing or correlating images for review. Moreover, current techniques may not offer sufficiently rapid compression and decompression of image files to satisfy increasing demands on system throughput rates and access times. Finally, alternative compression and decompression techniques do not offer the desired compression ratios, in combination with rapid compression and decompression in a client-server environment.

Another drawback of existing compression techniques is the storage, access and transmission of large data files even when a user cannot or does not desire to view the reconstructed image in all available detail. For example, in medical imaging, extremely detailed images may be acquired and stored, while a radiologist or physician who desires to view the images may not have a view port capable of displaying the images in the resolution in which they are stored. Thus, transmission of the entire images to a remote viewing station, in relatively time consuming operations, may not provide any real benefit and may slow reading or other use of the images. Furthermore, only certain portions of a medical image may be relevant for diagnosis or treatment. Thus, considerable storage space in a PACS may be allocated to the storage of medical image data that is irrelevant for the patient's diagnosis and treatment. This problem becomes even more acute as imaging systems achieve greater and greater resolutions, which correspond to a need for even more data storage space.

There is a need, therefore, for an improved image data compression and decompression technique which provides rapid compression and decompression of image files, and which obtains improved compression ratios and transmission times. In addition, there also is a need for a technique which permits compressed image data files to be created and transmitted in various resolutions or sizes, depending upon the bandwidth and desired or available resolution on a client side. Furthermore, there is a particular need for a technique to enable image data storage systems to accommodate the increase in data required to store medical images obtained with ever increasing resolutions of imaging systems.

BRIEF DESCRIPTION

A technique is presented for selecting portions of a medical image data set to be stored and portions of the medical image data set to be discarded or processed differently in order to reduce the overall amount of image data that is stored for each image data set. The selection is based on the clinical purpose for obtaining the medical image data. The clinical purpose for obtaining the medical image is used to define the regions of interest in the medical image. The regions of interest may be stored at their full resolution, while the remaining portions of the medical image are stored at a lesser resolution.

The medical image is typically obtained by scanning a patient using an imaging system. The regions of interest in the medical image are segmented from the other regions of the image based on the clinical purpose for obtaining the medical image. The regions of interest are then extracted from the medical image data and used to create a segmentation list, or "seglist". For three dimensional image data, the segmentation list is a three-dimensional bit mask of the outcome of the segmentation results. The seglist and the original medical image are then decomposed into multiple resolution levels. Each resolution level has a low frequency component and several high frequency components. The low frequency portions at each resolution level are stored in their entirety. However, not all of the high frequency components at each resolution level are stored. Some of the high frequency components at each resolution level may be discarded or stored in a format that reduces storage needs. The seglist is used to select the regions in the high frequency portions of the multi-resolution image data to be stored. Those regions in the high frequency portions of the multi-resolution image data that correspond to a region of interest as established by the bit mask are stored. Those regions in the high frequency portions of the multi-resolution image data that do not correspond to regions of interest as established by the bit mask are discarded, or may be stored in an alternative manner that required less data storage.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
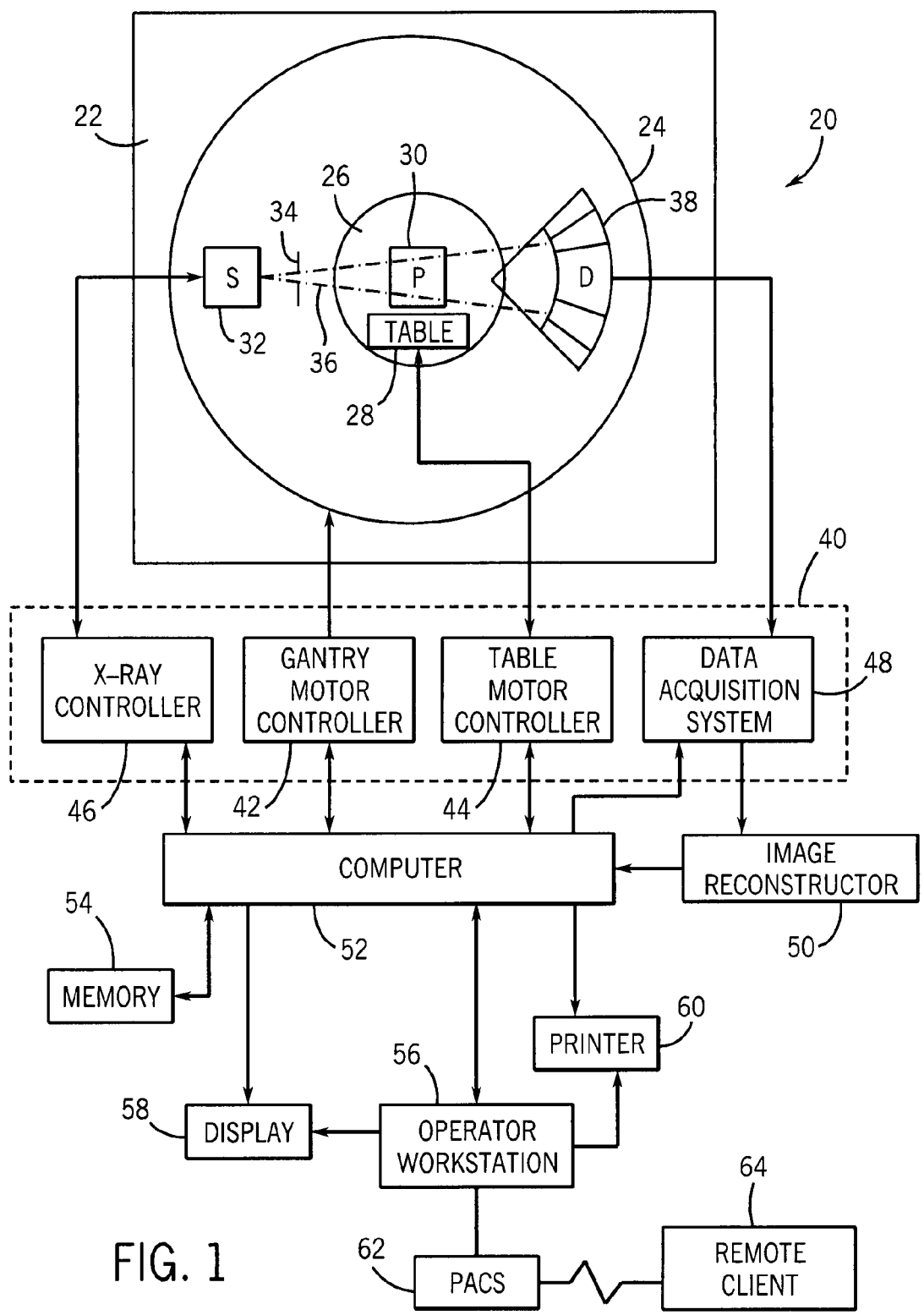
FIG. 1 is a schematic drawing of an exemplary imaging system, in this case a computed tomography ("CT") imaging system, designed to implement the enhanced image data storage scheme in accordance with an exemplary embodiment of the present technique.

Referring now to FIG. 1, the present invention will be described as it might be applied in conjunction with an exemplary imaging system, in this case a computed tomography (CT) imaging system. In general, however, it should be borne in mind that the present techniques may be used with image data produced by any suitable imaging modality. In a typical application, the imaging system may be designed both to acquire original image data and to process the image data for display and analysis is presented. As noted below, however, in certain applications the image data acquisition and subsequent processing (e.g., for the transformations and compression described below) may be carried out in physically separate systems or work stations. The illustrated embodiment of the CT imaging system 20 has a frame 22, a gantry 24, and an aperture (imaging volume or CT bore volume) 26. A patient table 28 is positioned in the aperture 26 of the frame 22 and the gantry 24. The patient table 28 is adapted so that a patient 30 may recline comfortably during the examination process.

The illustrated embodiment of the CT imaging system 20 has an X-ray source 32 positioned adjacent to a collimator 34 that defines the size and shape of the X-ray beam 36 that emerges from the X-ray source 32. In typical operation, the X-ray source 32 projects a stream of radiation (an X-ray beam) 36 towards a detector array 38 mounted on the opposite side of the gantry 24. All or part of the X-ray beam 36 passes through a subject, such as a patient 30, prior to impacting the detector array 38. It should be noted that all or part of the x-ray beam 36 may traverse a particular region of the patient 30, such as the liver, pancreas, heart, and so on, to allow a scan of the region to be acquired. The detector array 38 may be a single slice detector or a multi-slice detector and is generally formed by a plurality of detector elements. Each detector element produces an electrical signal that represents the intensity of the incident X-ray beam 36 at the detector element when the x-ray beam 36 strikes the detector array 38. These signals are acquired and processed to reconstruct an image of the features within the patient 30.

The gantry 24 may be rotated around the patient 30 so that a plurality of radiographic views may be collected along an imaging trajectory described by the motion of the X-ray source 32 relative to the patient 30. In particular, as the X-ray source 32 and the detector array 38 rotate along with the gantry 24, the detector array 38 collects photons resulting from X-ray beam attenuation at the various view angles relative to the patient 30 and produces signals or data representative of the incident photons. Data collected from the detector array 38 then undergoes pre-processing and filtering to condition the data to represent the line integrals of the attenuation coefficients of the scanned patient 30. The processed data, commonly called projections, are then filtered and back projected to formulate an image of the scanned area. Thus, an image or slice is acquired which may incorporate, in certain modes, less or more than 360 degrees of projection data, to formulate an image.

Rotation of the gantry 24 and operation of the X-ray source 32 are controlled by a system controller 40, which furnishes both power and control signals for CT examination sequences. Moreover, the detector array 38 is coupled to the system controller 40, which commands acquisition of the signals generated in the detector array 38. The system controller 40 may also execute various signal processing and filtration functions, such as for initial adjustment of dynamic ranges, interleaving of digital image data, and so forth. In general, system controller 40 commands operation of the imaging system 20 to execute examination protocols and to process acquired data. In the present context, system controller 40 also includes signal processing circuitry, typically based upon a general purpose or application-specific digital computer, associated memory circuitry for storing programs and routines executed by the computer, as well as configuration parameters and image data, interface circuits, and so forth. The system controller 40 includes a gantry motor controller 42 that controls the rotational speed and position of the gantry 24 and a table motor controller 44 that controls the linear displacement of the patient table 28 within the aperture 26. In this manner, the gantry motor controller 42 rotates the gantry 24, thereby rotating the x-ray source 32, collimator 34 and the detector array 38 one or multiple turns around the patient 30. Similarly, the table motor controller 44 displaces the patient table 28, and thus the patient 30, linearly within the aperture 26. Additionally, the X-ray source 32 may be controlled by an X-ray controller 46 disposed within the system controller 40. Particularly, the X-ray controller 46 may be configured to provide power and timing signals to the X-ray source 32.

In the illustrated embodiment, the system controller 40 also includes a data acquisition system 48. In this exemplary embodiment, the detector array 38 is coupled to the system controller 40, and more particularly to the data acquisition system 48. The data acquisition system 48 typically receives sampled analog signals from the detector array 38 and converts the data to digital signals for subsequent processing. An image reconstructor 50 coupled to the computer 52 may receive sampled and digitized data from the data acquisition system 48 and performs high-speed image reconstruction. Alternatively, reconstruction of the image may be done by the computer 52. Once reconstructed, the image produced by the imaging system 10 reveals internal features of the patient 30.

The data collected by the data acquisition system 48, or the reconstructed images, may be transmitted to the computer 52 and to a memory 54. It should be understood that any type of memory to store a large amount of data may be utilized by such an exemplary imaging system 10. Also the computer 52 may be configured to receive commands and scanning parameters from an operator via an operator workstation 56 typically equipped with a keyboard and other input devices. An operator may control the CT imaging system 20 via the operator workstation 56. Thus, the operator may observe the reconstructed image and other data relevant to the system from computer 52, initiate imaging, and so forth.

The CT imaging system 20 also has a display 58 that is coupled to the operator workstation 56 and the computer 52 and may be utilized by a user to observe the reconstructed image, as well as to provide an interface for control of the operation of the CT imaging system 20. In this embodiment, a printer 60 is present to enable a hard copy of a medical image to be printed. In the illustrated embodiment, the CT imaging system 20 is coupled to a picture archiving and communications system (PACS) 62 via the operator workstation 56 for long-term storage of image data. It should be noted that the PACS 62 may be coupled to a remote system 64, such as radiology department information system (RIS), hospital information system (HIS) or to an internal or external network, so that others at different locations may gain access to the image and to the image data. However, access to the image data may also be obtained remotely through the PACS 62.

It should be further noted that the computer 52 and operator workstation 56 may be coupled to other output devices, such as a standard or special purpose computer monitor and associated processing circuitry. One or more operator workstations 56 may be further linked in the CT imaging system 20 for outputting system parameters, requesting examinations, viewing images, and so forth. In general, displays, printers, workstations, and similar devices supplied within the CT imaging system 20 may be local to the data acquisition components, or may be remote from these components, such as elsewhere within an institution or hospital, or in an entirely different location, linked to the imaging system CT via one or more configurable networks, such as the Internet, virtual private networks, and so forth.

As noted above, it should be borne in mind that the CT system referred to herein is merely one exemplary source of image data that may be handled in accordance with the present techniques. Most such systems will include operator interfaces and software specifically adapted to acquire image data and to at least partially process the data in accordance with the specific physics of the imaging modality. Indeed, other arrangements of CT systems, other reconstruction techniques, and so forth may give rise to image data that may be managed as described herein.

Figure 2:
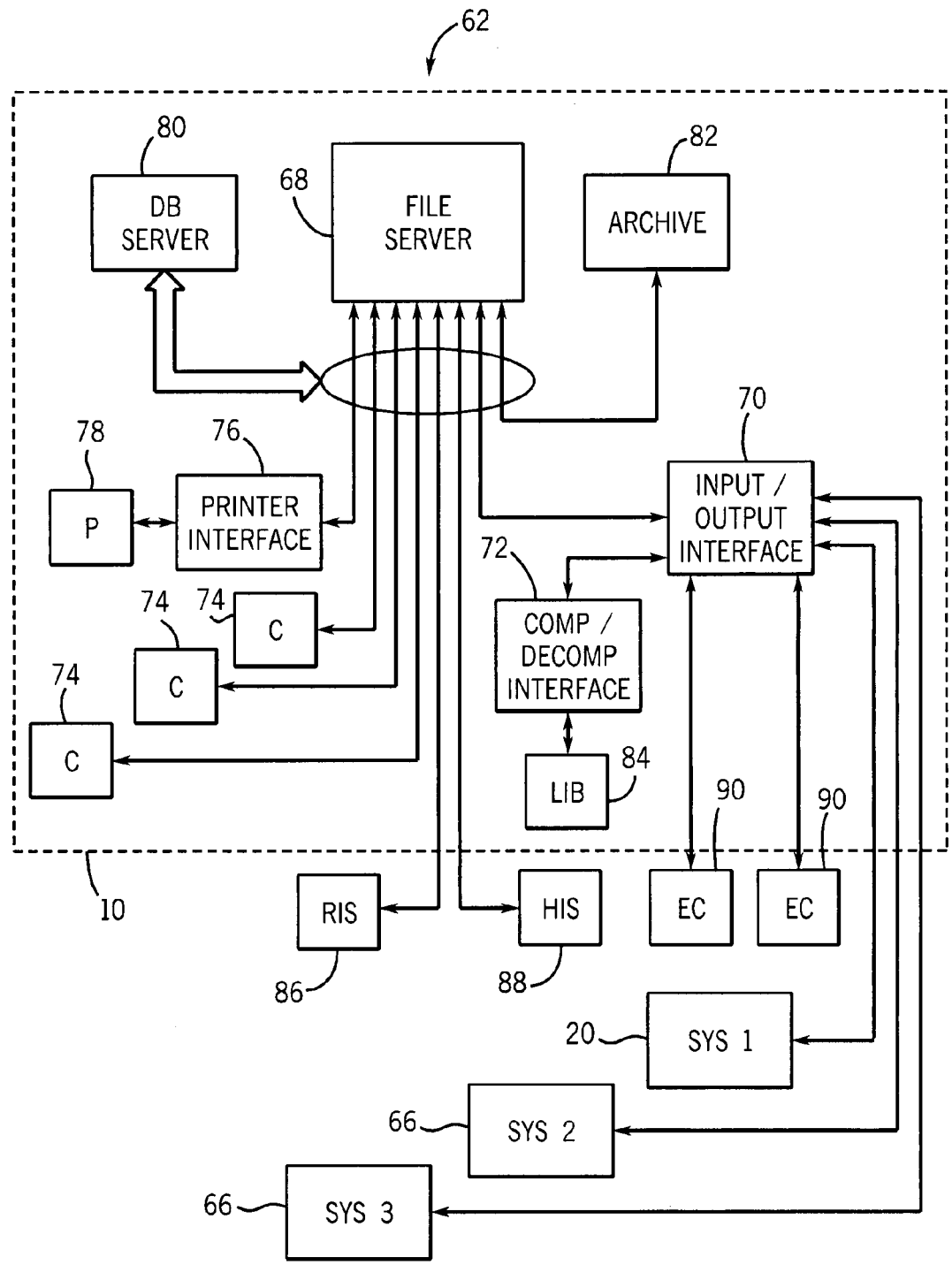
FIG. 2 is a diagrammatical representation of a picture archiving and communication system, or PACS, for receiving and storing image data from the imaging system of FIG. 1, in accordance with an exemplary embodiment of the present technique.

Referring generally to FIG. 2, an exemplary embodiment of a PACS 62 for receiving, compressing and decompressing image data is presented. In the illustrated embodiment, the CT imaging system 20 is used for short-term storage of image data only. Memory 54 of the CT imaging system 20 is limited and cannot be used to store image data with any degree of permanence, particularly when the system is used to carry out examinations for a large number of patients in a clinic, hospital or other institution. For example, data space occupied by old image data may be written over by new image data. The PACS 62 is used for long-term storage of medical image data. In the illustrated embodiment, PACS 62 receives image data from CT imaging system 20, as well as several other separate imaging systems designated by reference numeral 66. As will be appreciated by those skilled in the art, the imaging systems may be of various type and modality, such as MRI systems, PET systems, radio fluoroscopy (RF), computed radiography (CR), ultrasound systems, digital X-ray systems, X-ray tomography systems, ultrasound systems, and so forth. Moreover, the systems may include processing stations or digitizing stations, such as equipment designed to provide digitized image data based upon existing film or hard copy images. It should also be noted that the systems supplying the image data to the PACS may be located locally with respect to the PACS, such as in the same institution or facility, or may be entirely remote from the PACS, such as in an outlying clinic or affiliated institution. In the latter case, the image data may be transmitted via any suitable network link, including open networks, proprietary networks, virtual private networks, and so forth.

PACS 62 includes one or more file servers 68 designed to receive and process image data, and to make the image data available for decompression and review. File server 68 receives the image data through an input/output interface 70. Image data may be compressed in routines accessed through a compression/decompression interface 72. As described more fully below, compression/decompression interface 72 serves to compress the incoming image data rapidly and optimally, while maintaining descriptive image data available for reference by file server 68 and other components of the PACS. Where desired, compression/decompression interface 72 may also serve to decompress image data accessed through the file server 68. The file server 68 is also coupled to internal clients, as indicated at reference numeral 74, each client typically including a work station at which a radiologist, physician, or clinician may access image data from the server, decompress the image data, and view or output the image data as desired. Clients 74 may also input information, such as dictation of a radiologist following review of examination sequences. Similarly, file server 68 may be coupled to one or more interfaces, such as a printer interface 76 designed to access and decompress image data, and to output hard copy images via a printer 78 or other peripheral.

A database server 80 is used to associate image data, and other work flow information within the PACS, by reference to one or more file servers 68. In the presently contemplated embodiment, database server 80 may include cross-referenced information regarding specific image sequences, referring or diagnosing physician information, patient information, background information, work list cross-references, and so forth. The information within database server 80 serves to facilitate storage and association of the image data files with one another, and to allow requesting clients to rapidly and accurately access image data files stored within the system. Similarly, file server 68 is coupled to one or more archives 82, such as an optical storage system, which serve as repositories of large volumes of image data for backup and archiving purposes. Techniques for transferring image data between file server 68, and any memory associated with file server 68 forming a short-term storage system, and archive 82, may follow any suitable data management scheme, such as to archive image data following review and dictation by a radiologist, or after a sufficient time has lapsed since the receipt or review of the image files.

In the illustrated embodiment, other components of the PACS system or institution may be integrated with the foregoing components to further enhance the system functionality. For example, a compression/decompression library 84 is coupled to compression/decompression interface 72 and serves to store compression routines, algorithms, look up tables, and so forth, for access by input/output interface 70 (or other system components) upon execution of compression and decompression routines (i.e. to store various routines, software versions, code tables, and so forth). In practice, compression/decompression interface 72 may be part of compression/decompression library 84. Library 84 may also be coupled to other components of the system, such as internal clients 74 or printer interface 76, serving similarly as a library or store for the compression and decompression routines and algorithms. Although illustrated as a separate component, it should be understood that compression/decompression library 84 may be included in any suitable server or memory device, including within file server 68. Moreover, code defining the compression and decompression processes described below may be loaded directly into compression/decompression interface 72 and/or compression/decompression library 84, or may be loaded or updated via network links, including wide area networks, open networks, and so forth.

Additional systems may be linked to the PACS, such as directly to server 80, or through interfaces such as input/output interface 70. In the embodiment illustrated in FIG. 2, a radiology department information system or RIS 86 is linked to file server 68 to facilitate exchanges of data, typically cross-referencing data within database server 80, and a central or departmental information system or database. Similarly, a hospital information system or HIS 88 may be coupled to database server 80 to similarly exchange database information, workflow information, and so forth. Where desired, such systems may be interfaced through data exchange software, or may be partially or fully integrated with the PACS system to provide access to data between the PACS database and radiology department or hospital databases, or to provide a single cross-referencing database. Similarly, external clients, as designated at reference numeral 90, may be interfaced with the PACS to enable images to be viewed at remote locations. Such external clients may employ decompression software, or may receive image files already decompressed by compression/decompression interface 72. Again, links to such external clients may be made through any suitable connection, such as wide area networks, virtual private networks, and so forth.

In the illustrated embodiment, the PACS 62 provides for multi-resolution (or multi-size) image data compression. Where a user does not desire to view a full image with maximum resolution, or where the user view port is limited, such multi-resolution image compression facilitates transfer of a reduced size image to the user for viewing, with excellent image quality. Moreover, the multi-resolution image compression may allow a user to view a reduced size or reduced resolution image relatively rapidly, and to "zoom" on the image thereafter by transfer of only a portion of the compressed data corresponding to components of the greater sized image not already transferred. The additional data is then processed and combined with the reduced size image data to obtain the larger sized image. In addition, the technique described below utilizes purpose-driven image data storage to reduce the amount of stored image data associated with an image stored in the PACS 62.

It should be noted that the processing and storage of the image data as described below may be performed in the PACS 62, or in any other suitable system component or components. The processing will typically be embodied in computer code that can be stored and executed on any one or more than one of the computers of the acquisition the PACS, an operator workstation, server, and so forth, so long as the system is capable of performing the computations involved.

The multi-resolution implementation may be based partially upon lossless integer wavelet decomposition. Specifically, as will be recognized by those skilled in the art, wavelet decomposition involves a dyadic filtering and sub-sampling process. This creates a hierarchical set of sub-bands. As will be discussed in more detail below, a wavelet transformed image data set includes low frequency components along with high frequency components, which may be considered as noise or variations from the low frequency components. A single level wavelet decomposition results in a decomposed data set which includes one low frequency sub-band LL, along with three high frequency ones LH, HL, and HH. Subsequent decomposition may be considered to produce a further data set in which the low frequency sub-band is further decomposed into a set of sub-bands, including a low frequency band, along with three additional high frequency sub-bands.

Figure 3:
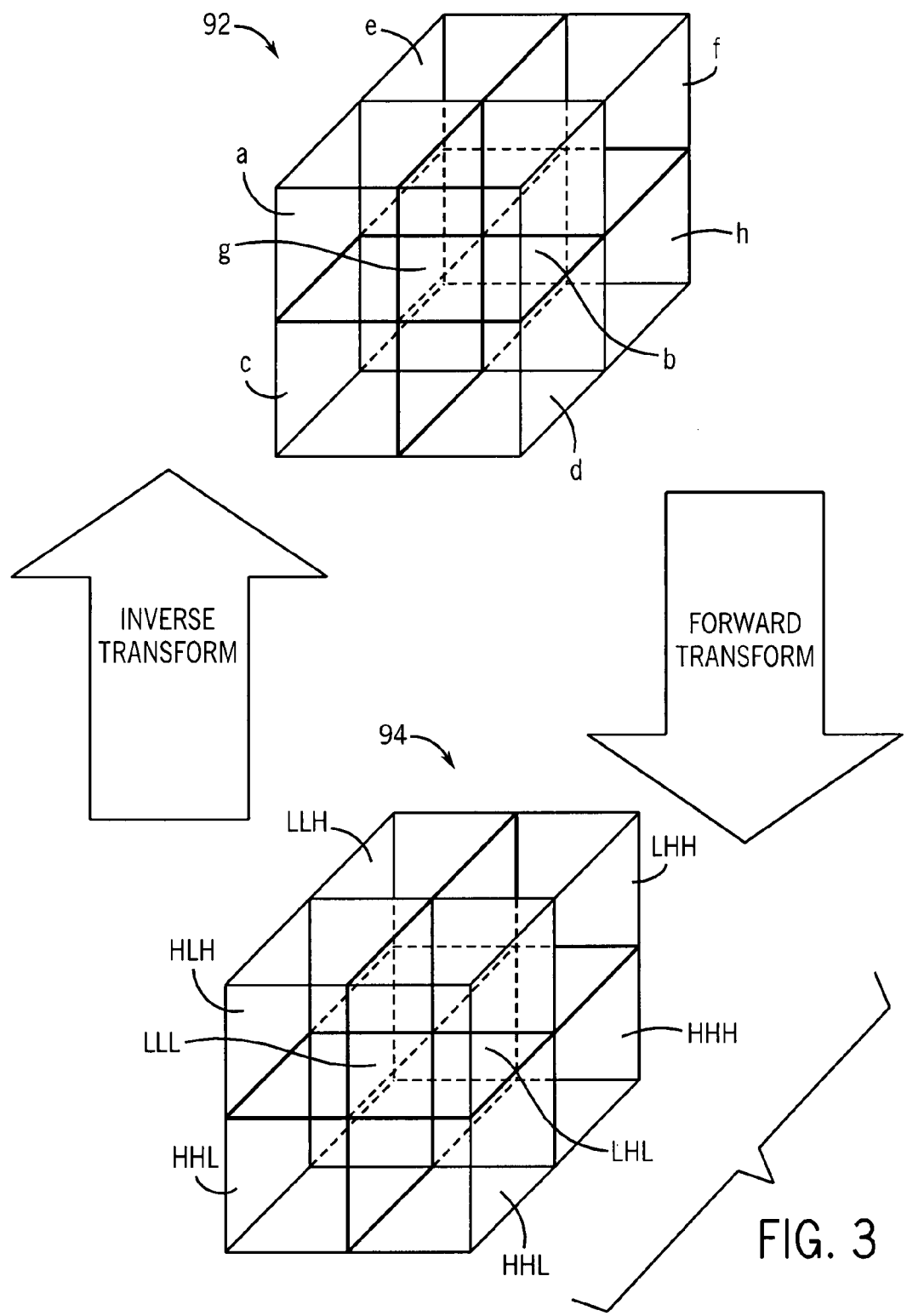
FIG. 3 is a representation of a volume of data transformed into a first level of decomposition using integer wavelet decomposition, in accordance with an exemplary embodiment of the present invention.

The wavelet transformation technique may be carried out on two dimensional or three dimensional (or higher dimension) data sets. FIG. 3 is generally a representation of a volume 92 of image data. The image data may be stored as a series of values representative of voxels in data blocks. The volume 92 is logically divided into eight subsets of data, indicated by letters a-h. Each subset (a-h) of data represents a portion of an object of interest, such as a portion of the patient 30.

As noted above, the data in the volume 92 may be represented in a multi-resolution format using lossless integer wavelet decomposition. A one step forward wavelet trans form in one dimension may, for example, be based on the following equations:

$$L(n)=\lfloor (C(2n)+C(2n+1))/2 \rfloor, \text{ for } n \in [0,N/2-1]; \text{ and}$$

and $$H(n)=C(2n)-C(2n+1),$$

where $C(i)$ for $i \in [0,N-1]$ represents the input data, L and H are the decomposed low and high frequency components and C is the input data. The "$\lfloor \ldots \rfloor$" operation produces the greatest integer less than the operands with "N" being the size of the input data. The converse of the one step forward wavelet transform is the one step inverse wavelet transform, which, in this example, is described by the following equations:

$$C(2n)=L(n)+\lfloor (H(n)+1)/2j; \text{ and}$$

$$C(2n+1)=C(2n)-H(n).$$

The equations for the forward and inverse wavelet transforms described above are for a one-dimensional single step transformation. A recursion of a single step wavelet transform is performed on the "LL" component at every level. The number of levels for the transformation is determined by fixing the row and/or column size of the smallest resolution. This level value is determined by the steps necessary to decompose the maximum of the row or column size of the original image to the desired smallest resolution size. If "n" is this level variable then the following equation is used, then:

$$n=\log_2(\max(\text{rows,cols}))-\log_2(d_{size}),$$

where "n" is the number of levels of decomposition, rows and columns are the original image dimensions, $\log_2$ is the log in base 2, and $d_{size}$ is the configurable size of the smallest resolution image.

In a two dimensional case, for example, the 2D forward transformation may be governed by the following equations:

$$LL=L\lfloor \lfloor L(a+b)/2 \rfloor + \lfloor (c+d)/2 \rfloor )/2 \rfloor;$$

$$HL=\lfloor ((a-b)+(c-d))/2 \rfloor;$$

$$LH=\lfloor (a+b)/2 \rfloor - \lfloor (c+d)/2 \rfloor; \text{ and}$$

$$HH=(a-b)-(c-d).$$

The inverse transform process works by taking the smallest resolution "LL" band and combining it with its associated "HL", "LH" and "1*H" bands to produce the next higher resolution. This process is repeated until either the full resolution of the image is achieved or a specified level of resolution is attained. The inverse transform is modular with respect to single level reconstruction, allowing users to specify a desired level, from the smallest resolution to full resolution, for reconstruction. The 2D inverse transform is, for the example provided above, governed by the following set of equations:

$$a=LL+\lfloor (HL+1)/2 \rfloor + \lfloor (LH+ \lfloor (HH+1)/2 \rfloor )+1)/2 \rfloor;$$

$$b=LL+\lfloor (HL+1)/2 \rfloor + \lfloor ((LH+ \lfloor (HH+1)/2 \rfloor )+1)/2 \rfloor -(LH+ \lfloor (HH+1)/2 \rfloor);$$

$$c=LL+\lfloor (HD+1)/2 \rfloor -HL+ \lfloor (LH+ \lfloor (HH+1)/2 \rfloor -HH+1)/2 \rfloor; \text{ and}$$

$$d=(LL+\lfloor (HL+1)/2 \rfloor -HL+\lfloor (LH+\lfloor (HH+1)/2 \rfloor -HH+1)/2 \rfloor)-((LH+\lfloor (HH+1)/2 \rfloor)-HH).$$

It should be noted, however, that these are intended to be exemplary transforms only, and that the present invention is not limited to use of any particular transform or compression algorithm.

Figure 4:
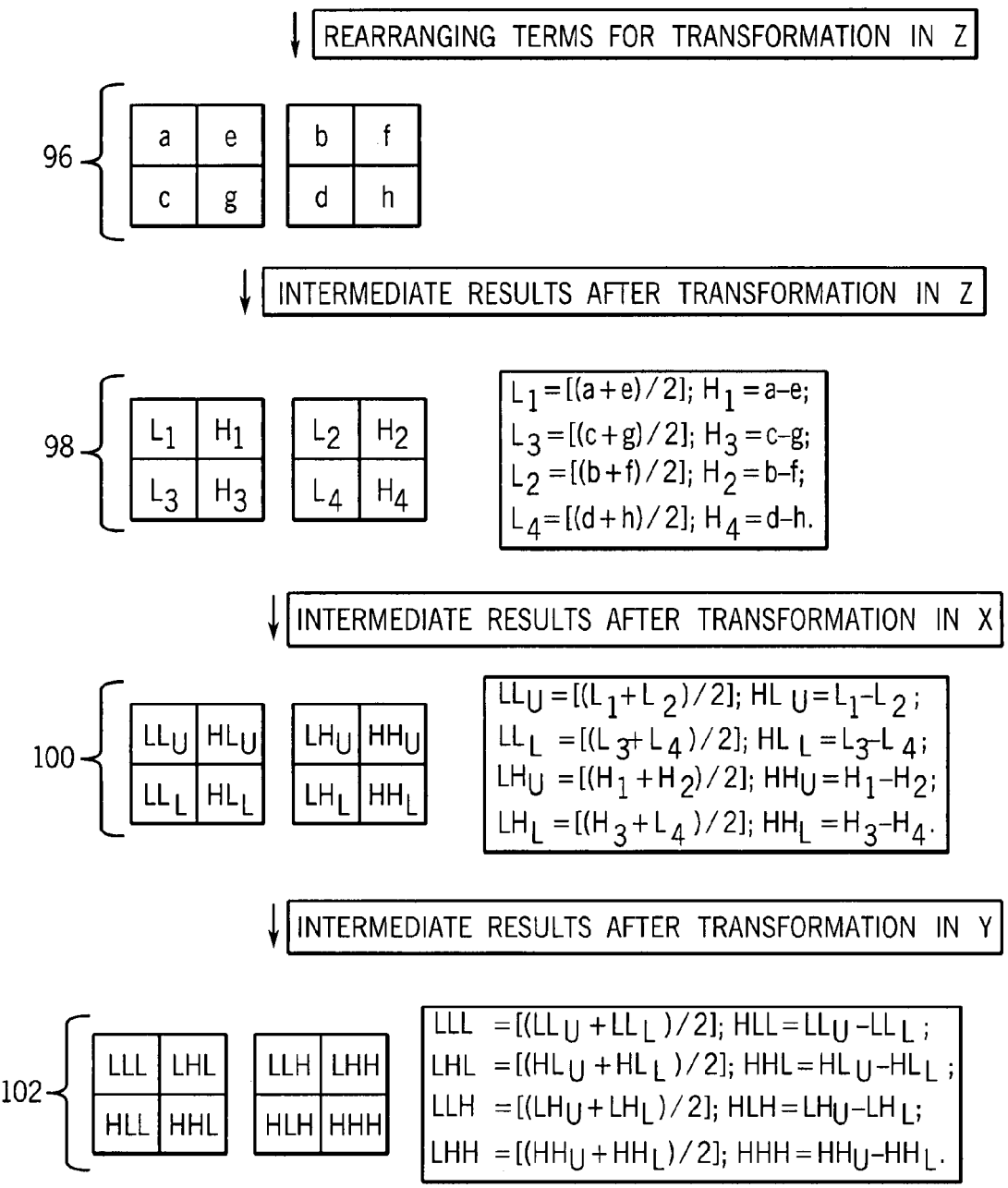
FIG. 4 is a representation of a forward transform process using integer wavelet decomposition, in accordance with an exemplary embodiment of the present invention.

Referring generally to FIGS. 3 and 4, a three-dimensional (3D) forward transform process using integer wavelet decomposition is presented. The transformation may be performed in any order as long as the forward and inverse transformations are performed in the reverse order with respect to each other. In this embodiment, the PACS 62 performs the forward transform process on the volume 92 of image data of FIG. 3 in the Z, X and then Y dimensions using an integer wavelet transform process, resulting in a first level transformation 94. However, the CT imaging system 20 may also be configured to perform this and the subsequent aspects of the image data compression technique. Input data 96 is a representation of the eight subsets of data a-h of the volume 92. The three-dimensional transform in the Z dimension, operating on the input data 96 and resulting in intermediate results 98, may be accomplished by the following equations:

$$L_1=\lfloor (a+e)/2) \rfloor;$$

$$H_1=a-e;$$

$$L_3=\lfloor (c+g)/2) \rfloor;$$

$$H_3=c-g;$$

$$L_2=\lfloor (b+f)/2) \rfloor;$$

$$H_2=b-f;$$

$$L_4=\lfloor (d+h)/2) \rfloor; \text{ and}$$

$$H_4=d-h.$$

The 3D transform in the X dimension, operating on the intermediate results 98 and resulting in intermediate results 100, may be accomplished by the following equations:

$$LL_U=\lfloor (L_1+L_2)/2) \rfloor;$$

$$HL_U=L_1-L_2;$$

$$LL_L=\lfloor (L_3+L_4)/2) \rfloor;$$

$$HL_L=L_3-L_4;$$

$$LH_U=\lfloor (H_1+H_2)/2) \rfloor;$$

$$HH_U=H_1-H_2;$$

$$LH_L=\lfloor (H_3+H_4)/2) \rfloor; \text{ and}$$

$$HH_L=H_3-H_4.$$

The 3D transform in the Y dimension, operating on the intermediate results 100 and resulting in intermediate results 102, may be accomplished by the following equations:

$$LLL=\lfloor (LL_U+LL_L)/2) \rfloor;$$

$$HLL=LL_U-LL_L;$$

$$LHL=\lfloor (HL_U+HL_L)/2) \rfloor;$$

$$HHL=HL_U-HL_L;$$

$$LLH=\lfloor (LH_U+LH_L)/2) \rfloor;$$

$$HLH=LH_U-LH_L;$$

$$LHH=\lfloor (HH_U+HH_L)/2) \rfloor; \text{ and}$$

$$HHH=HH_U-HH_L.$$

Intermediate results 102 represent a first level of decomposition, pictorially illustrated as the first level transformation 94 of FIG. 3. The forward transform of FIG. 4 may be repeated for additional levels of decomposition, facilitating the integer wavelet multi-resolution (IWMR) framework. For example, the LLL block may be logically divided into a-h as in the volume 92 of FIG. 3. In this embodiment, the PACS 62 performs the forward transform on the volume LLL in the Z, X and Y dimensions using the integer wavelet forward transform process, resulting in a second level of decomposition and a third level of decomposition.

Figure 5:
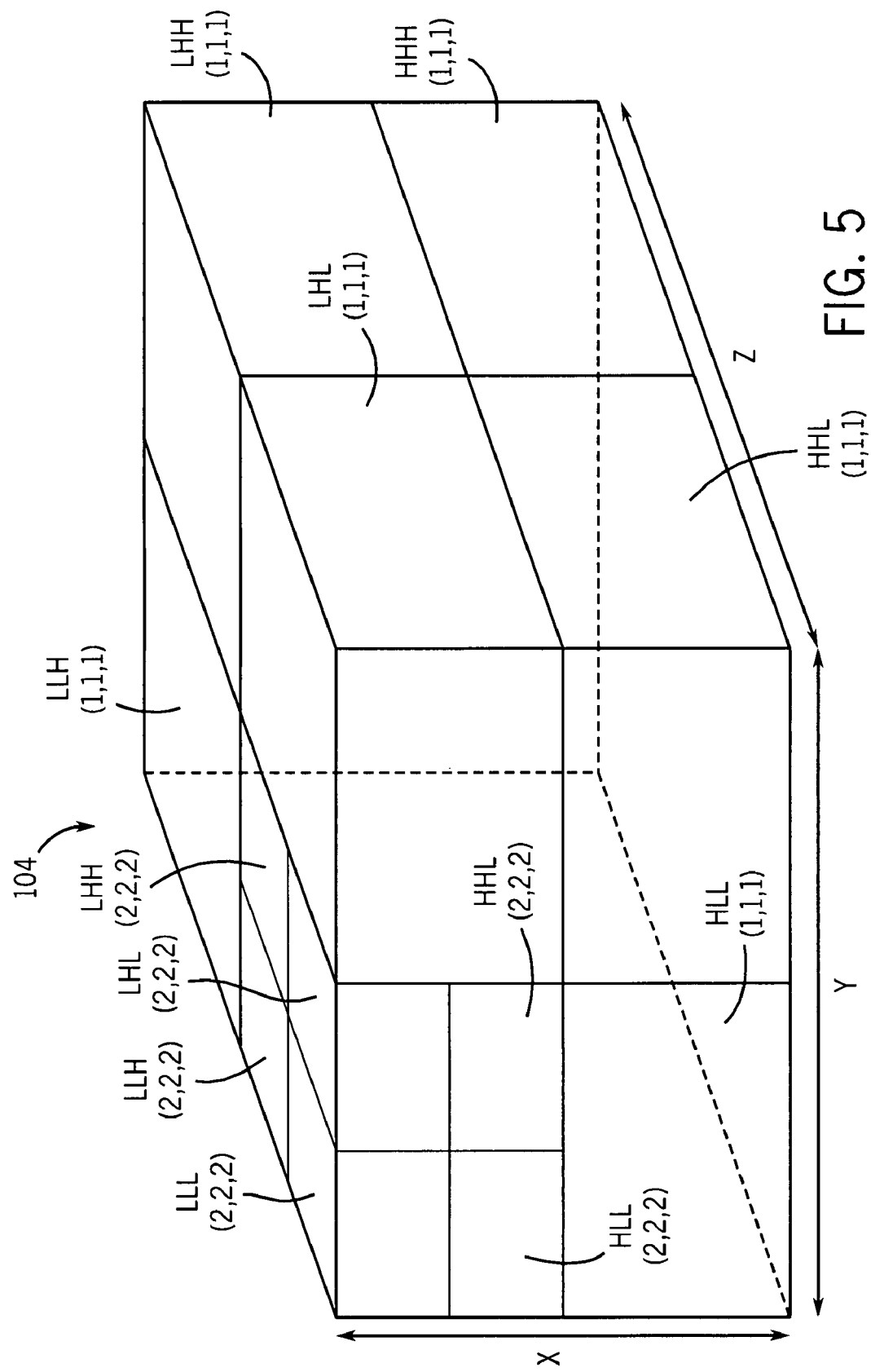
FIG. 5 is a representation of a multi-resolution data set after a second level of decomposition using integer wavelet decomposition, in accordance with an exemplary embodiment of the present invention.

Referring generally to FIG. 5, the reorganization of data for a multi-level decomposition of a 3D volumetric data set after a second level of decomposition is presented, represented generally by reference numeral 104. In this view, two resolution levels are illustrated. In this example, the volume 92 of FIG. 3 was decomposed using the equations of FIG. 4 to form the first level of decomposition. Similarly, the subset LLL of FIG. 3, which may be represented as LLL (1, 1, 1), was decomposed to form a second level of decomposition, which includes one low frequency sub-band LL (2, 2, 2), along with three high frequency ones LH (2, 2, 2), HL (2, 2, 2), and HH (2, 2, 2).

Figure 6:
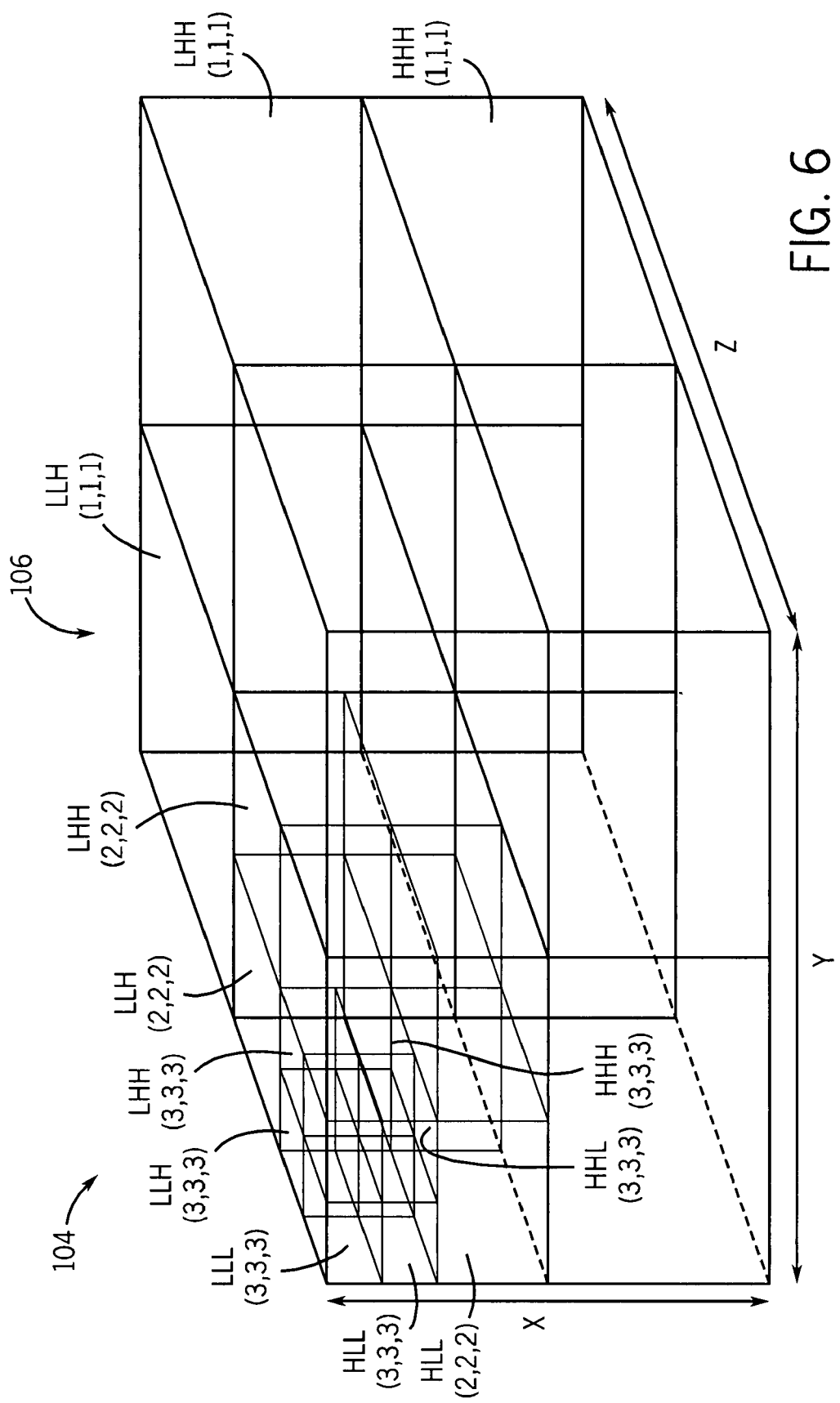
FIG. 6 is a representation of a multi-resolution data set after a third level of decomposition using integer wavelet decomposition, in accordance with an exemplary embodiment of the present invention.

Referring generally to FIG. 6, the reorganization of data for a multi-level decomposition of a 3D volumetric data set after a third level of decomposition is presented, referenced generally by reference numeral 106. The subset LLL (2,2,2) was decomposed to form a third level of decomposition, which includes one low frequency sub-band LL (3, 3, 3), along with three high frequency ones LH (3, 3, 3), HL (3, 3, 3), and HH (3, 3, 3). The multi-resolution framework of FIGS. 5 and 6 enables very large amounts of data to be managed. In previous systems, the data would then be compressed before storage in the PACS 62. However, this technique is problematic with the large amounts of data produced with the ever-increasing resolutions of medical imaging systems. Therefore, the present technique is used to reduce the amount of data associated with each image data set that is stored in the PACS 62.

Figure 7:
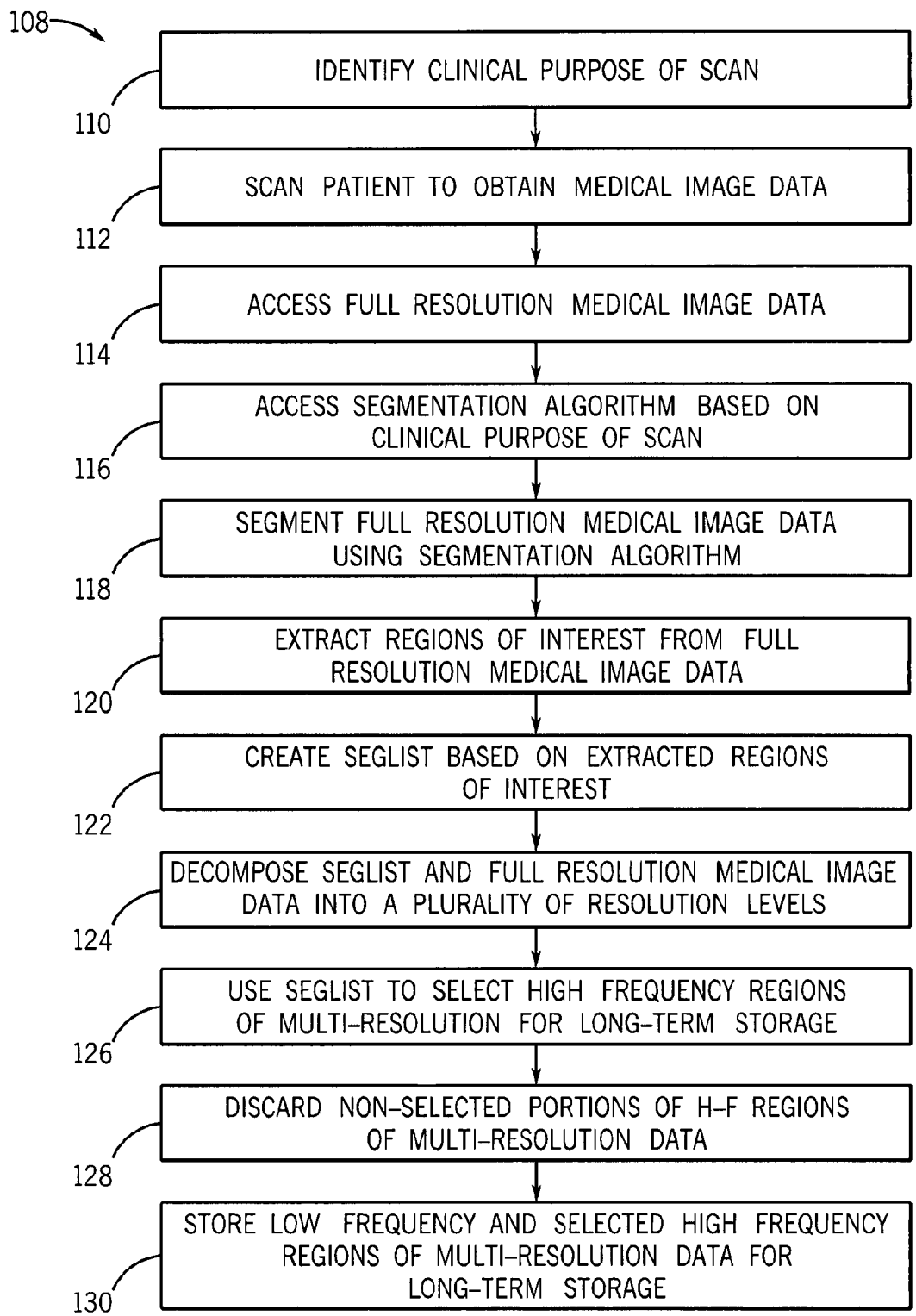
FIG. 7 is a block diagram of a technique for selectively storing medical image data based on the clinical purpose of the image, in accordance with an exemplary embodiment of the present invention.

Referring generally to FIG. 7, a technique is presented for selectively storing multi-resolution image data based on the clinical purpose of the image, represented generally by reference numeral 108. The technique enables the amount of medical image data that is stored in the PACS 62 for each data set to be reduced. The regions of the high frequency portions of the medical image that are the most important, as defined by the clinical purpose for the scan, are stored in the PACS 62. However, the regions of the high frequency portions of the medical image that are not important, as defined by the clinical purpose for the scan, are discarded and, thus, not stored in the PACS 62, or may be processed or stored in an alterative manner, such as via lossy compression.

The technique calls for identifying the clinical purpose of the scan, as represented generally by block 110. The clinical purpose of the scan may be for any of a myriad of clinical purposes, such as an angiogram analysis, a mammogram analysis, a perfusion quantification, tumor detection and/or follow up, aneurysm detection, blocked blood vessels detection and quantification, etc, in a particular portion of the body. A system operator may select the purpose from a menu or list or purposes, thereby directing the system to automatically execute the steps of the technique. In general, the purpose will be known or available from the instructions or prescription provided by the physician who ordered the examination sequence (e.g., for detection of a particular medical condition, pathology, and so forth).

The patient is then scanned via the imaging system (e.g., CT system 20 described above, or any other modality system) to obtain medical image data, represented generally by block 112. The medical image data that is obtained from scanning the patient is typically obtained at a single resolution, ideally the highest, or greatest, resolution available from the imaging system. As noted above, this technique is applicable for use with imaging systems other than the CT imaging system 20.

The full resolution medical image data is accessed by the PACS 62, represented generally by block 114. In practice, some filtering, processing and the like may be performed on the image data prior to forwarding it to the PACS. Moreover, as noted above, the processing described below may be performed by the PACS itself, or by an upstream component prior to storage of the image data in the PACS. Similarly, the data stored in the PACS may be processed as described below, to reduce memory needs, and then restored to the PACS. The full resolution medical image data is typically sent to the PACS 62 from the imaging system, such as CT imaging system 20. In this embodiment, the CT imaging system 20 is not used for long-term storage of medical image data. Long-term storage of medical image data occurs in the PACS 62. However, in other embodiments of the present technique, an imaging system may be used for long-term storage of medical image data.

The PACS 62 (or more generally, the component carrying out the segmentation process) accesses a segmentation algorithm that is operable to segment regions of interest in the medical image data from regions of lesser interest based on the clinical purpose of the scan, as represented by block 116. Depending on the clinical purpose of the scan, one or more anatomical features may be of great interest in one medical image and of no interest in another medical image. For example, if the purpose of the scan is to enable a radiologist to look for tumors in the lung, anatomical features other than the lungs (e.g., surrounding tissues) would be of lesser interest. Therefore, in this example, a segmentation algorithm would be selected that is operable to segment lung tissues from other tissues.

The segmentation algorithm is then used to segment the regions of interest from the other regions of the medical image, represented generally by block 118. The PACS 62 may use a copy of the original image data for segmentation purposes.

The regions of interest are then extracted from the medical image data set, as represented generally by block 120. The PACS 62 may use a copy of the original image data for extracting the regions of interest from the medical image data set. As will be appreciated by those skilled in the art, a large number of such segmentation algorithms are available for various anatomies, conditions, and so forth. The segmentation algorithm will typically be adapted to the anatomy or type of tissue, and specific algorithms may differ, depending upon the modality originating the image data. In practice, the particular segmentation algorithm selected and applied may be the result of operator intervention (e.g., interaction of a human operator at a workstation coupled to the PACS). Alternatively the segmentation algorithm selection and execution process may be partially or fully automated. Moreover, some algorithms may require or benefit from selections, settings, and options that may be made by a human operator, particularly considering the purpose for which the images were acquired (e.g., the anatomical features or conditions desired to be evaluated by a radiologist or other physician).

The extracted regions of interest are then used to create a segmentation list, or seglist, as represented generally by block 122. For a three dimensional image, the segmentation list is a three-dimensional run length encoded bit mask of the outcome of the segmentation results. A two dimensional image, similarly, gives rise to a two dimensional seglist. The bit mask is encoded in a stream of ones and zeroes using standard techniques. That is, the mask is typically a binary map of the image, indicating which pixels or voxels are designated as included in the features of interest, and which are not. In a presently contemplated implementation, the portions of the seglist that correspond to the regions of interest are labeled with a "one" and the other regions are labeled with a "zero".

The seglist and the original medical image are then decomposed into a multiple resolution levels, as represented generally by block 124. The seglist decomposition parallels the decomposition of the original medical image.

The seglist is used to select regions in the high frequency portions of the multi-resolution image data to be stored in long-term storage, as represented generally by block 126. That is, in a presently contemplated implementation, those regions in the high frequency portions of the multi-resolution image data that correspond to a region in the bit mask of the seglist having a "one" are stored by the PACS 62. The low frequency version of that region of the image also is stored.

Those pixels or voxels of the high frequency portions of the multi-resolution image data that are not selected for long-term storage may be discarded or processed or stored in a different manner, as represented generally by block 128. In one embodiment presently contemplated, those regions in the high frequency portions of the multi-resolution image data that correspond to a region in the bit mask of the seglist having a "zero" are not stored by the PACS 62. Instead, the data in those regions is discarded, thereby reducing the amount of data to be stored. However, the low frequency version of that region of the image is stored.

The low frequency portions of the multi-resolution image data and the selected portions of the high frequency image data are compressed and stored in long-term storage, as represented generally by block 130. Thus, the complete low frequency component at each resolution level in the multi-resolution image data is stored. In addition, the regions of the high frequency components that correspond to the regions of interest as defined by the clinical purpose for the image are stored. Therefore, when viewing the medical image data at one of the three resolution levels described above, the regions of interest will be at the highest resolution available at that resolution level. The other regions of the image will be at a lower resolution.

Figure 8:
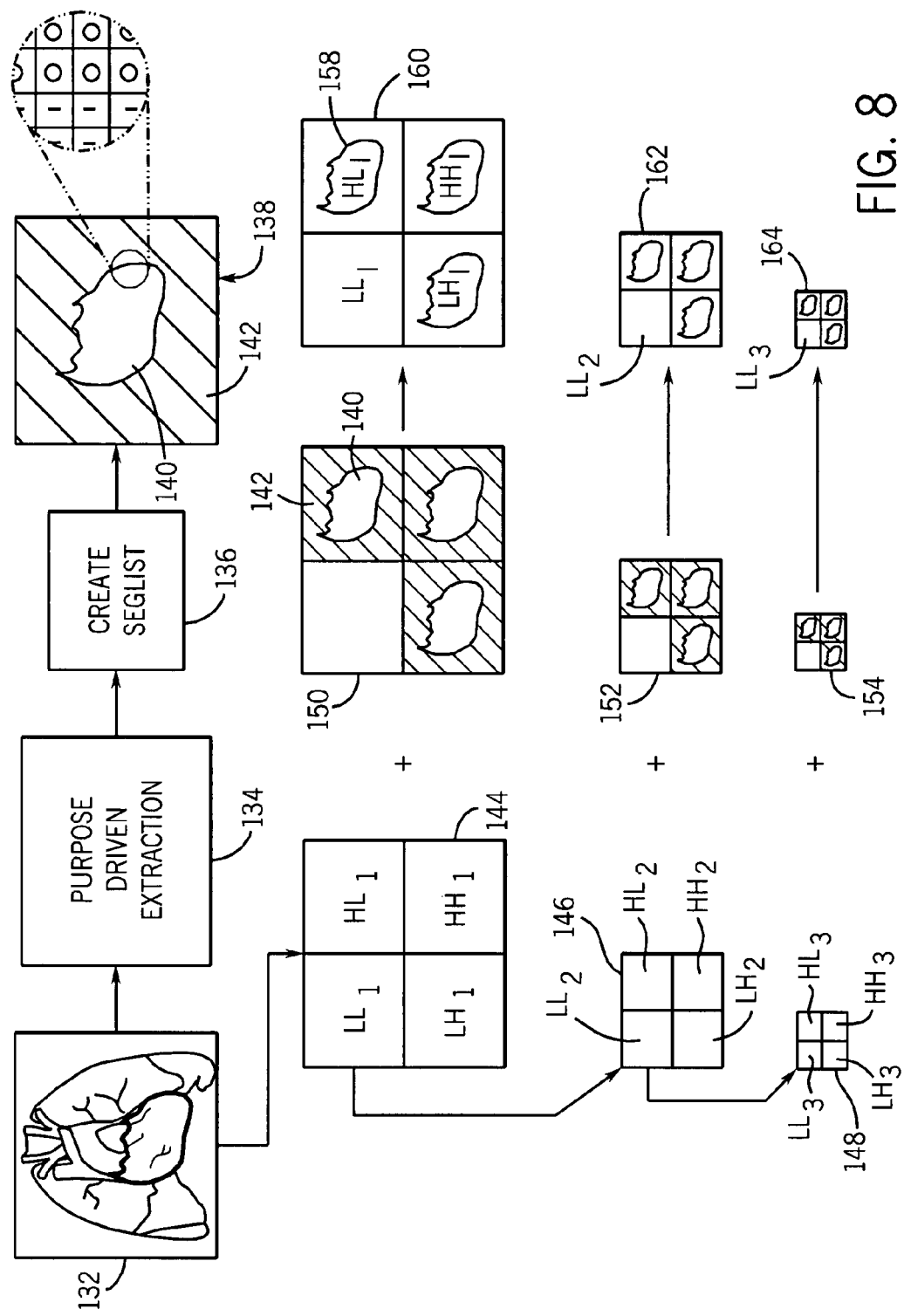
FIGS. 8 and 9 are diagrammatic representations of a technique for selectively storing medical image data based on the clinical purpose of the image, in accordance with an exemplary embodiment of the present invention.
Figure 9:
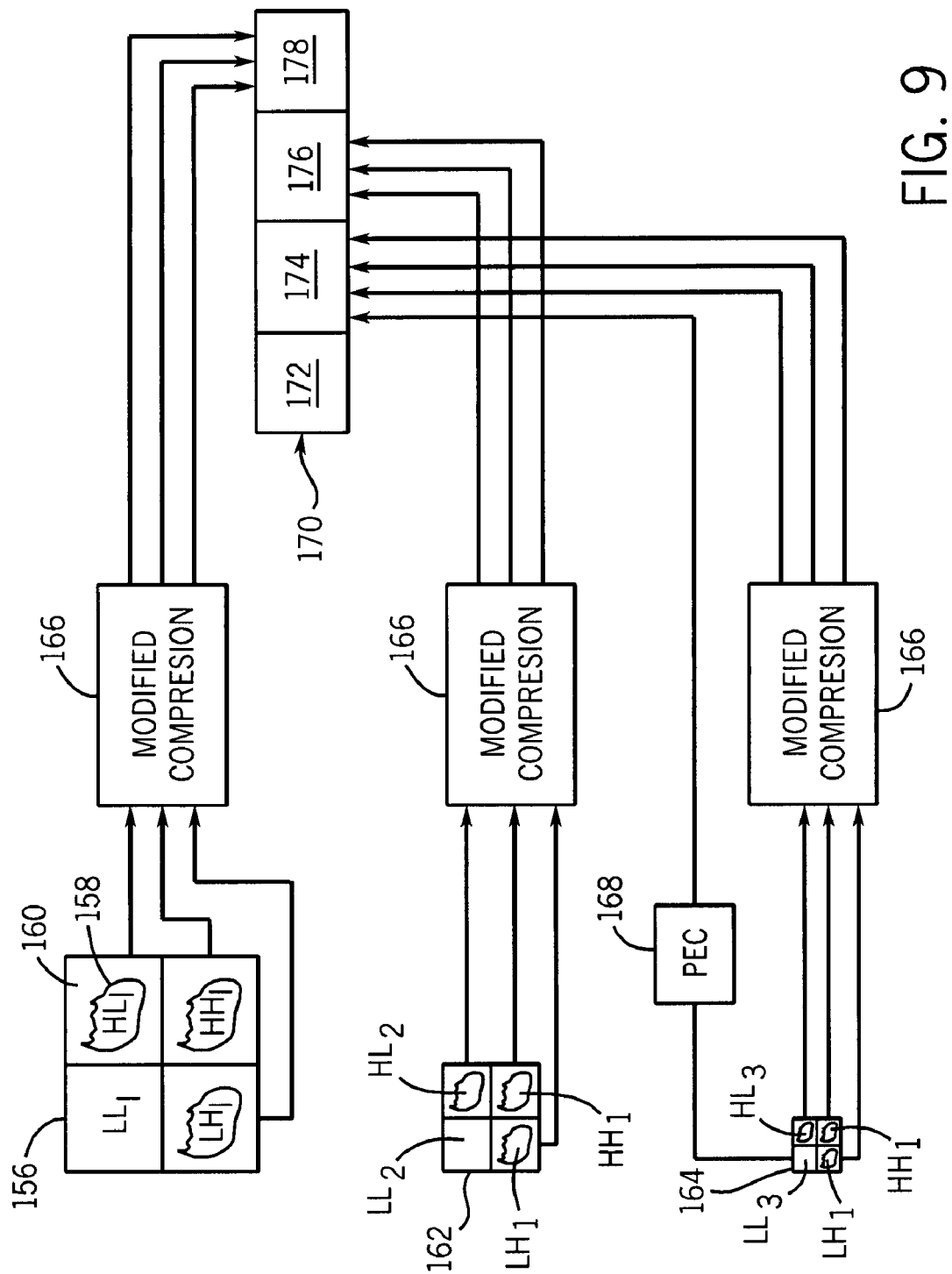

Referring generally to FIGS. 8 and 9, diagrammatic representations of portions of the technique of FIG. 7 are presented. First, original medical image data 132 at full resolution is accessed. The representation of the original medical image data 132 is shown in two dimensions for clarity. However, the original medical image data 132 may comprise medical image data in three dimensions. In this example, the original image 132 is an image of the cardiac region of a patient, including the heart, blood vessels, and portions of the lungs. In this example, the clinical purpose for obtaining the image is to examine the heart. Purpose-driven segmentation and extraction of the original image 132 is performed as described in the technique above.

In this example, a patient's heart is segmented and extracted from the other anatomical features in the full resolution image of the patient's cardiac region, represented generally by reference numeral 134. This is followed by the act of creating a seglist based on the extracted heart, represented generally by reference numeral 136. A representative example of a region corresponding to pixels or voxels noted in a seglist 138 is shown. As with the original medical image data 132, the seglist 138 occupies three dimensions. The seglist will differ from one patient to the next because the volumes of the hearts will vary from patient to patient (or even for a single patient at different points in time). The seglist 138 comprises a bit mask of ones and zeroes that effectively form a window portion 140 and a blocking portion 142. The window portion 140 corresponds to the regions of interest in the original medical image data 132. In particular, the window portion 140 corresponds to the regions of the high frequency decomposed image data to be stored in long-term storage in the PACS 62. In this example, the window portion 140 corresponds to the volume of the extracted heart. The blocking portion 142 corresponds to areas of lesser importance. In particular, the blocking portion 142 corresponds to the portions of the high frequency decomposed data that are to be discarded. The window portion 140 and blocking portion 142 comprise voxels having values of one and zero, respectively. In a present implementation, the "ones" and "zeroes" signify to the PACS 62 whether to save the corresponding voxels of the original image or to discard them.

In this example, the original full resolution image is decomposed three times using integer wavelet transformation to form three different resolution versions of the image. After the first transformation, a first decomposed image data set 144 of the medical image data is produced. The first decomposed image data set 144 has a low frequency portion, $LL_1$, and three high frequency portions: $LH_1$, $HH_1$, and $HL_1$. The low frequency portion, $LL_1$, is decomposed to produce a second decomposed image data set 146 of the medical image data. The second decomposed image data set 146 has a low frequency portion, $LL_2$, and three high frequency portions: $LH_2$, $HH_2$, and $HL_2$. The low frequency portion, $LL_2$, of the second decomposed version 146 is decomposed to produce a third decomposed image data set 148 of the medical image data. The third decomposed image data set 148 also has a low frequency portion, $LL_3$, and three high frequency portions: $LH_3$, $HH_3$, and $HL_3$. Each decomposed version of the medical image data has greater resolution. Thus, the first decomposed image data set 144 has the lowest resolution and the third decomposed image data set 148 has the greatest resolution.

In this example, the seglist is also decomposed three times using integer wavelet transformation to form three different resolution versions of the seglist: a first decomposed seglist 150, a second decomposed seglist 152, and a third decomposed seglist 154. Thus, each resolution of the decomposed image data sets 144, 146, 148 has a corresponding decomposed seglist 150, 152, 154 with the same resolution.

In this embodiment, the PACS 62 receives the first decomposed image data set 144 and the first decomposed seglist 150 and produces a first purpose-driven image data set 156 that is stored in long-term storage in the PACS 62. The decomposed seglists 150, 152, 154 are used to establish the portions of the high frequency portions of the decomposed image data sets 144, 146, 148 to be stored in the PACS 62. Only the high frequency components of the decomposed seglists 150, 152, 154 are used. Thus, the low frequency portion, $LL_1$, of the first purpose-driven image data set 156 is the same as the low frequency portion, $LL_1$, of the first decomposed image data set 144. The regions of the high frequency portions, $LH_1$, $HH_1$, and $HL_1$, of the first decomposed image data set 144 that correspond to the regions of the window portions 140 of the first decomposed seglist 150 are included in the first purpose-driven image data set 156, represented by reference numeral 158. The regions of the high frequency portions, $LH_1$, $HH_1$, and $HL_1$, of the first decomposed image data set 144 that correspond to the blocking portions 142 of the first decomposed seglist 150 are discarded and are not included in the first purpose-driven image data set 156. These blank regions of the high frequency portions, $LH_1$, $HH_1$, and $HL_1$, of the first purpose-driven image data set 156 are represented by reference numeral 160. Similarly, the PACS 62 produces a second purpose-driven image data set 162 and a third purpose-driven image data set 164 that correspond to the other two resolutions of the decomposed image data sets and decomposed seglists.

The purpose-driven image data sets 156, 162, 164 are compressed by a modified compression routine 166. Because the low frequency data for each higher level is further decomposed, information descriptive of these data sets is preserved in the lower levels, with the exception of the lower-most low frequency data set (i.e., $LL_3$ of the third decomposed image data set 148). In the present embodiment, the low frequency data set, $LL_3$, of the third purpose-driven image data set 164, which corresponds to $LL_3$ of the third decomposed image data set 148 is compressed using a predictive error compression technique 168.

Following compression of the high frequency and low frequency data sets, the resulting data is compiled in a data stream or file as indicated by reference numeral 170. In the illustrated embodiment, the data stream 170 includes a descriptive header 172 followed by a series of data sets, including a first set 174 for the third purpose-driven image data set 164, a second set 176 for the second purpose-driven image data set 162, and a third set 178 for the first purpose-driven image data set 156. The data stream 170 is sent to long-term storage where it is stored.

Figure 10:
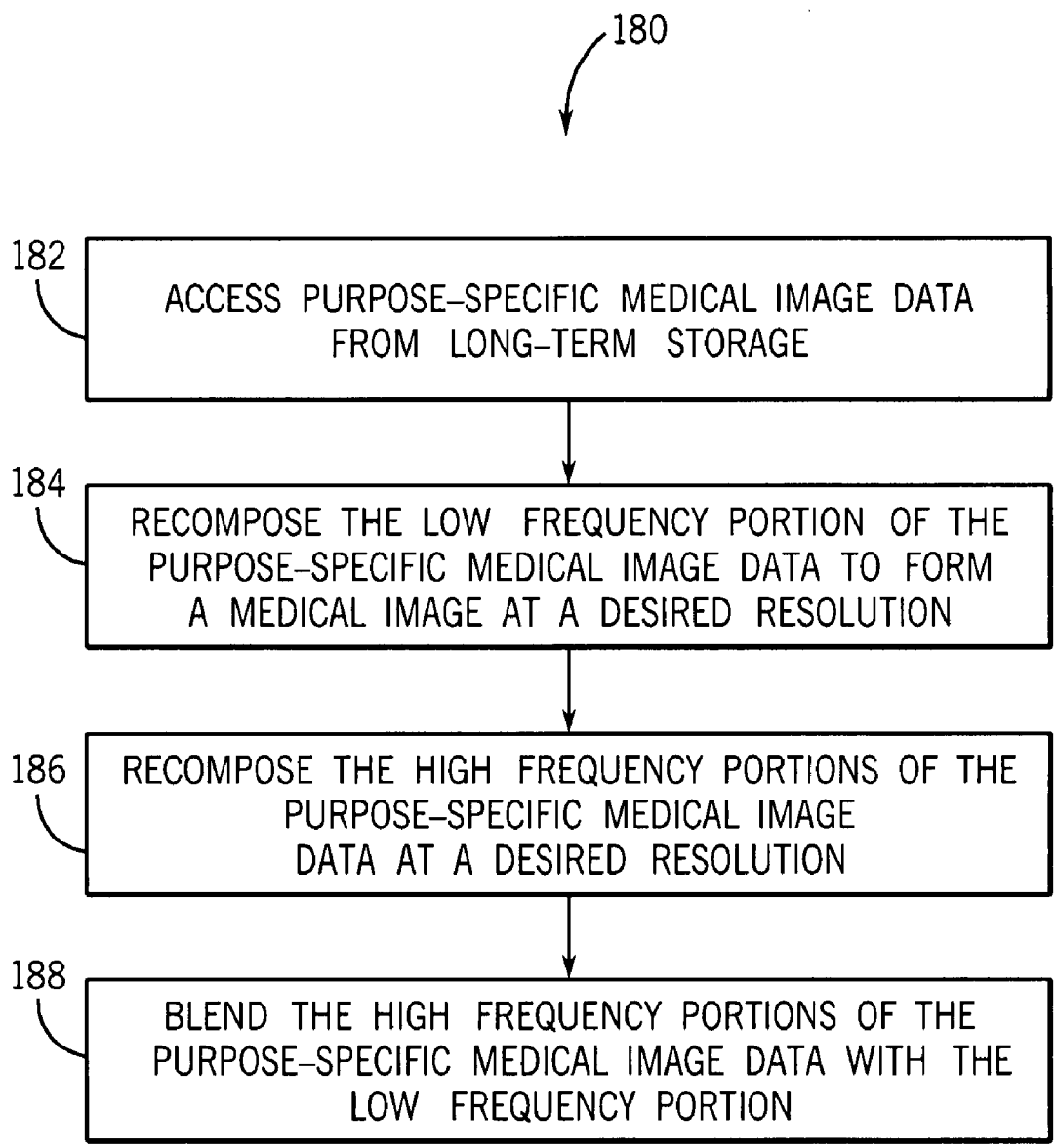
FIG. 10 is a block diagram of a technique for producing a medical image produced from selectively stored medical image data, in accordance with an exemplary embodiment of the present invention.

Referring generally to FIG. 10, a block diagram of a technique for producing a medical image from a purpose-driven image data set that has been compressed and stored in long-term storage is presented, represented generally by reference numeral 180. An image could be produced from any one of the resolution levels of the purpose-driven image data sets 156, 162, 164 in this manner. A purpose-driven image data set is accessed from the long-term storage, represented generally by block 182. The low frequency portion of the purpose-driven image data set is recomposed to form a medical image, represented generally by reference numeral 184. The high frequency portions of the purpose-driven image data set are also recomposed to form a medical image, represented generally by reference numeral 186. Then, the low frequency portion and the high frequency portions of the purpose-driven image data set are blended to form a medical image, represented generally by block 188.

Figure 11:
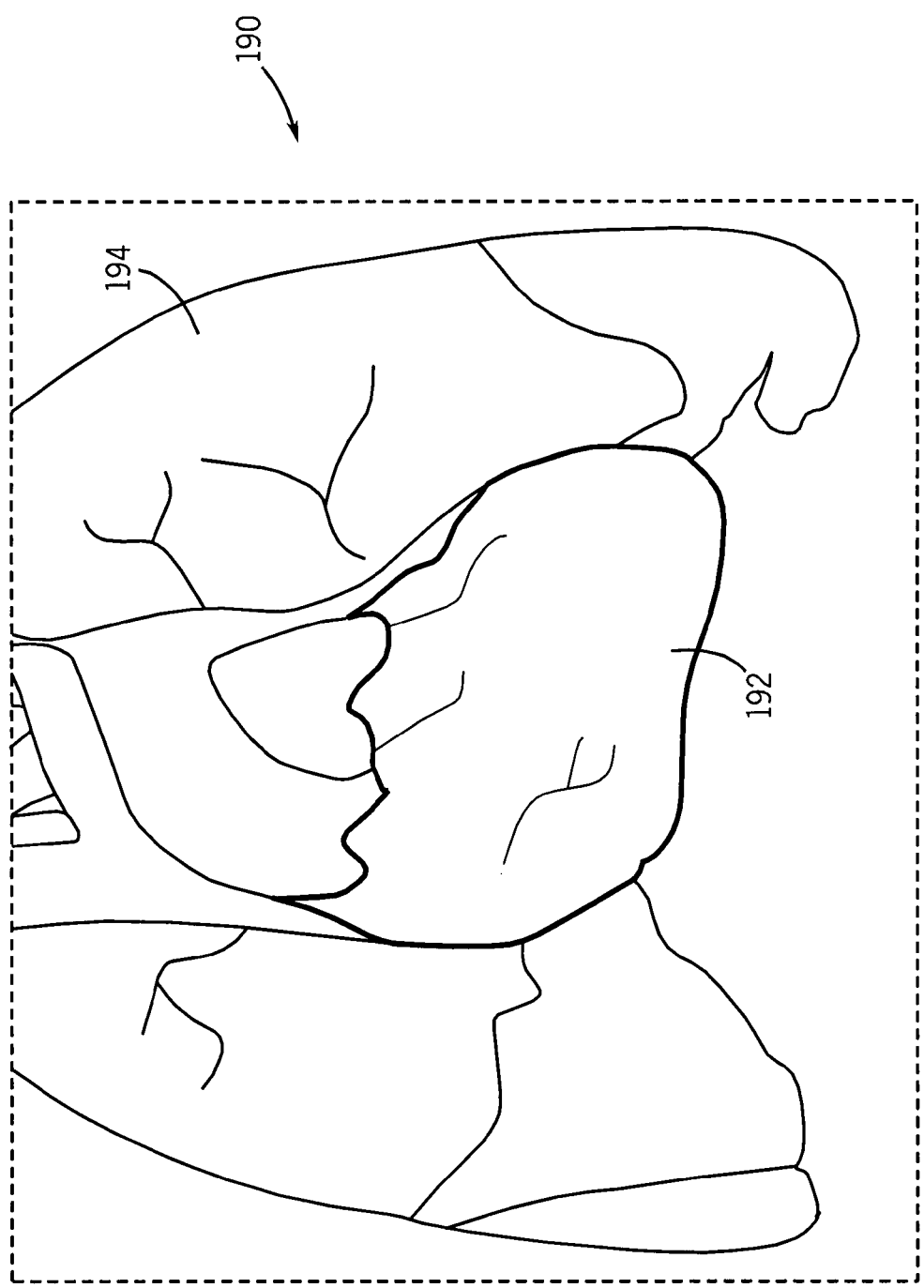
FIG. 11 is a representation of a medical image produced from selectively stored medical image data in accordance with the techniques described herein.

Referring generally to FIG. 11, a representation of a medical image produced from a purpose-driven image data set that has been compressed and stored in long-term storage is presented in accordance with the technique of FIG. 10 is presented, represented generally by reference numeral 190. A first portion 192 of the image 190 is produced from low frequency data and high frequency data. This first portion 192 is the region of interest as defined by the purpose of the scan. In addition, this corresponds to the window portions of the seglists. A second region 194 is produced from low frequency data only. This portion of the image corresponds to the mask portions of the seglist.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A computer-implemented method for processing image data, comprising:
    accessing image data comprising at least three dimensions of image data obtained by an imaging system;
    segmenting the image data to create segmented image data comprising at least three dimensions of image data;
    creating a segmentation list to identify a region of interest in the segmented image data based on the purpose for obtaining the image data;
    transforming the image data and the segmentation list into a plurality of resolution levels of image data comprising at least three dimensions of image data;
    identifying the regions of interest within the plurality of resolution levels of image data based on the segmentation list; and
    storing the regions of interest for each resolution level of the plurality of resolution levels.

2. The computer-implemented method for processing image data as recited in claim 1, wherein the segmentation list comprises a run-length encoded binary bitstream.

3. The computer-implemented method for processing image data as recited in claim 1, wherein transforming the image data into a plurality of resolution levels comprises performing a plurality of wavelet transformations of the image data.

4. The computer-implemented method for processing image data as recited in claim 1, wherein each resolution level of the plurality of resolution levels comprises a low frequency component and a plurality of high frequency components.

5. The computer-implemented method for processing image data as recited in claim 4, wherein storing image data comprises storing in long-term storage the high frequency components that correspond to the regions of interest for each of the plurality of resolution levels.

6. The computer-implemented method for processing image data as recited in claim 1, wherein identifying a region of interest comprises using a binary mask having a plurality of resolution levels to identify regions of the high frequency components that correspond to the regions of interest for each of the plurality of resolution levels.

7. The computer-implemented method for processing image data as recited in claim 6, comprising:
    preventing a region of image data that does not correspond to the region of interest from being stored.

8. The computer-implemented method for processing image data as recited in claim 1, comprising:
    storing in long-term storage a low frequency component for each resolution level of the plurality of resolution levels.

9. The computer-implemented method for processing image data as recited in claim 8, comprising:
    compressing a low frequency component and high frequency components that correspond to the regions of interest for each of the plurality of resolution levels prior to storage.

10. The computer-implemented method for processing image data as recited in claim 1, wherein identifying a region of interest from the image data based on a purpose for obtaining the image data comprises segmenting the region of interest within the image data using a segmentation algorithm selected from a plurality of segmentation algorithms based on the purpose for obtaining the image data.

11. The computer-implemented method for processing image data as recited in claim 10, comprising:
    extracting the region of interest from the segmented image data to create a binary mask, wherein the binary mask comprises a plurality of pixels or voxels, pixels or voxels corresponding to the region of interest having a first binary value and pixels or voxels outside the region of interest having a second binary value.

12. The computer-implemented method for processing image data as recited in claim 11, comprising:

transforming the binary mask into a plurality of resolution levels corresponding to the plurality of resolution levels of the image data.

13. A system for processing image data, comprising:
means for accessing image data comprising at least three dimensions of image data obtained by an imaging system;
means for segmenting the image data to create segmented image data comprising at least three dimensions of image data;
means for creating a segmentation list to identify a region of interest in the segmented image data based on the purpose for obtaining the image data;
means for transforming the image data and the segmentation list into a plurality of resolution levels of image data comprising at least three dimensions of image data;
means for identifying the regions of interest within the plurality of resolution levels of image data based on the segmentation list; and
means for storing the regions of interest for each resolution level of the plurality of resolution levels.

14. A machine-readable medium for processing medical image data, comprising:
code operable for accessing image data comprising at least three dimensions of image data obtained by an imaging system;
code operable for segmenting the image data to create segmented image data comprising at least three dimensions of image data;
code operable for creating a segmentation list to identify a region of interest in the segmented image data based on the purpose for obtaining the image data;
code operable for transforming the image data and the segmentation list into a plurality of resolution levels of image data comprising at least three dimensions of image data;
code operable for identifying the regions of interest within the plurality of resolution levels of image data based on the segmentation list; and
code operable for storing the regions of interest for each resolution level of the plurality of resolution levels.

15. A computer-implemented method for storing image data, comprising:
accessing image data from an imaging system;
segmenting the image data into segmented image data;
accessing a knowledge database operable to identify a region of interest in the segmented image data from among the plurality of regions of segmented image data based on a purpose for obtaining the image data;
creating a segmentation list of regions of interest in the segmented image data;
transforming the segmented image data and the segmentation list into a plurality of resolution levels;
identifying the regions of interest within the plurality of resolution levels in the image data based on the segmentation list.

16. The computer-implemented method for processing image data as recited in claim 15, wherein the segmentation list comprises a run-length encoded binary bitstream.

17. The computer-implemented method for processing image data as recited in claim 15, comprising:
storing the regions of interest for each resolution level of the plurality of resolution levels.

* * * * *

UNITED STATES PATENT AND TRADEMARK OFFICE
CERTIFICATE OF CORRECTION

PATENT NO. : 7,970,203 B2  Page 1 of 1
APPLICATION NO. : 11/725244
DATED : June 28, 2011
INVENTOR(S) : Avinash et al.

It is certified that error appears in the above-identified patent and that said Letters Patent is hereby corrected as shown below:

In Column 9, Line 3, delete "$L(n)=L(C(2n)+C(2n+1))/2\rfloor$, for $n \in [0,N/2-1]$;" and insert -- $L(n) = \lfloor(C(2n)+C(2n+1))/2\rfloor$, for n ∈ [0,N/2-1]; --, therefor.

In Column 9, Line 16, delete "$C(2n)=L(n)+L(H(n)+1)/2j$;" and insert -- $C(2n) = L(n) + \lfloor(H(n)+1)/2\rfloor$; --, therefor.

In Column 9, Line 37, delete "$LL=L\lfloor(L(a+b)/2)\rfloor+\lfloor(c+d)/2\rfloor)/2\rfloor$;" and insert -- $LL = \lfloor(\lfloor(a+b)/2)\rfloor+\lfloor(c+d)/2\rfloor)/2\rfloor$; --, therefor, In Column 9, Line 46, delete ""1*H"" and insert -- "HH" --, therefor.

In Column 9, Lines 59-60, delete "$c=LL+\lfloor(HD+1)/2\rfloor-HL+\lfloor(LH+\lfloor(HH+1)/2\rfloor-HH+1)/2\rfloor;$ and " and insert -- $c = LL +\lfloor(HL+1)/2\rfloor - HL +\lfloor (LH+\lfloor(HH+1)/2\rfloor - HH + 1)/2 \rfloor;$ and --, therefor.

In Column 10, Line 57, delete "$HHL=HL_I-HL_L$;" and insert -- $HHL= HL_U - HL_L$; --, therefor.

Signed and Sealed this
Tenth Day of April, 2012

David J. Kappos
*Director of the United States Patent and Trademark Office*